United States Patent [19]
Cobb et al.

[11] Patent Number: 5,989,566
[45] Date of Patent: Nov. 23, 1999

[54] STABLE VACCINE COMPOSITIONS FOR PARENTERAL ADMINISTRATION, A METHOD FOR THEIR USE, AND A PROCESS FOR THEIR PREPARATION

[75] Inventors: Ramune Marija Cobb; Christopher Leigh Schwartzkoff, both of New South Wales, Australia

[73] Assignee: American Cyanamid Company, Madison, N.J.

[21] Appl. No.: 08/672,786

[22] Filed: Jun. 28, 1996

Related U.S. Application Data

[60] Provisional application No. 60/000,605, Jun. 30, 1995.

[51] Int. Cl.$^6$ .......................... A61K 45/00; A61K 39/02
[52] U.S. Cl. ...................... 424/278.1; 424/184.1; 424/247.1; 424/239.1; 424/245.1; 424/255.1; 424/93.41; 424/93.4; 514/28; 514/30; 514/450; 549/264
[58] Field of Search ............................ 424/184.1, 247.1, 424/278.1, 239.1, 245.1, 255.1, 93.41, 93.4; 514/28, 30, 450; 549/264

[56] References Cited

U.S. PATENT DOCUMENTS

| | | |
|---|---|---|
| 3,885,011 | 5/1975 | Renoux et al. . |
| 4,292,307 | 9/1981 | Zemlyakova . |
| 4,606,918 | 8/1986 | Allison et al. . |
| 4,988,824 | 1/1991 | Maulding et al. . |
| 5,262,400 | 11/1993 | Chu et al. . |
| 5,387,598 | 2/1995 | Rossignol et al. . |

FOREIGN PATENT DOCUMENTS

| | | |
|---|---|---|
| 2030043 | 8/1979 | Australia . |
| 2050830 | 5/1980 | Australia . |
| 0388239B1 | 1/1995 | European Pat. Off. . |
| 1171125 | 11/1969 | United Kingdom . |
| 2 267 707 | 12/1993 | United Kingdom . |

OTHER PUBLICATIONS

Kirk–Othmer: Encyclopedia of Chemical Technology, Third Ed., pp. 793–796.

Umehara, et al., Compatibility Between Doramectin and Foot–and–mouth Disease Vaccine Administered Simultaneously in Cattle., Brazil. J. Vet. Parasitol., vol. 2, No. 2, 1993, pp. 141–144.

*Primary Examiner*—Anthony C. Caputa
*Assistant Examiner*—Khalid Masood
*Attorney, Agent, or Firm*—Barbara L. Renda

[57] ABSTRACT

The invention relates to certain stable vaccine compositions comprising a macrocyclic lactone compound, a milbemycin compound, an avermectin compound or mixtures thereof; at least one antigen; a dispersing agent; an adjuvant; a water soluble organic solvent; and saline or water or mixtures thereof. The invention further relates to stable compositions as described above of a macrocyclic lactone compound, a milbemycin compound, an avermectin compound or mixtures thereof, but without an antigen. The invention also relates to a method for preventing or controlling helminthiasis, infection by acarids and arthropod endo-and ectoparasites and bacterial and viral disease in warm-blooded animals by the parenteral administration of compositions of the invention. The invention further relates to a process for the preparation of the invention compositions.

18 Claims, No Drawings

STABLE VACCINE COMPOSITIONS FOR PARENTERAL ADMINISTRATION, A METHOD FOR THEIR USE, AND A PROCESS FOR THEIR PREPARATION

This patent application claims the benefit of prior U.S. Provisional application Ser. No. 60/000605, filed Jun. 30, 1995.

BACKGROUND OF THE INVENTION

Macrolide compounds including macrocyclic lactones such as LL-F28249α-λ compounds, 23-oxo or 23-imino derivatives of LL-F28249α-λ compounds, milbemycin compounds such as milbemycin D and milbemycin oxime, avermectin compounds such as abamectin, ivermectin and doramectin, and mixtures thereof are useful for the prevention and control of helminthiasis and infection by acarids and arthropod endo- and ectoparasites in warm-blooded animals. Subcutaneous injection of aqueous compositions is one of the preferred methods for administering those compounds.

Vaccines are used to protect warm-blooded animals from a variety of diseases and are also administered by subcutaneous injection. However, a vaccine composition containing both a macrolide compound and antigens is not known. The primary reason for the lack of such a combination vaccine is due to the fact that aqueous injectable compositions of macrolide compounds contain dispersing agents which are known to interact with proteins and affect the permeability of the outer membrane of bacterial cells. Such interaction can denature or otherwise disrupt proteins such as antigens.

GB-A-2030043 describes injectable compositions which comprise tetramisole or its levorotatory isomer and a vaccine. However, that application does not disclose a combination vaccine which includes a complex macrolide compound. Further, that application does not describe the use of a dispersing agent, an important component in aqueous macrolide injectable compositions.

It is therefore an object of the present invention to provide stable vaccine compositions comprising macrolide compounds and antigens. It is also an object to provide stable compositions of macrolide compounds in the absence of an antigen.

It is also an object of the present invention to provide a method for preventing or controlling helminthiasis, infection by acarid and arthropod endo- and ectoparasites and bacterial and viral disease in warm-blooded animals.

It is a further object of the present invention to provide a process for the preparation of stable vaccine compositions.

These and other objects and features of the present invention will become more apparent from the detailed description thereof set forth below.

SUMMARY OF THE INVENTION

The present invention relates to stable vaccine compositions. The compositions comprise, on a weight to volume basis, about 0.05% to 2.5% of a macrolide compound as hereinafter defined; about 0.1% to 6% of a water soluble organic solvent; about 1% to 8% of a dispersing agent; about 10% to 50% of an adjuvant; at least one antigen; up to about 0.1% of a preservative; and saline or water or a mixture thereof.

Surprisingly, it has been found that the vaccine compositions of the present invention are stable in the presence of a dispersing agent and may be stored for prolonged periods of time without loss of antigen and macrolide potency.

DETAILED DESCRIPTION OF THE INVENTION

In accordance with the present invention, the stable vaccine compositions comprise a macrolide compound as hereinafter defined, a water soluble organic solvent; a dispersing agent; an adjuvant; at least one antigen; optionally, a preservative, and saline or water or a mixture thereof. The invention also provides a method for protecting or controlling helminthiasis, infection by acarid and arthropod endo- and ectoparasites and disease in warm-blooded animals.

Preferred stable vaccine compositions of the present invention comprise, on a weight to volume basis, about 0.1% to 1% of an LL-F28249α-λ compound, a 23-oxo or 23-imino derivative of an LL-F28249α-λ compound, a milbemycin compound, an avermectin compound or mixtures thereof; about 0.2% to 2.5% of a water soluble organic solvent; about 2% to 7% of a dispersing agent; about 20% to 40% of an adjuvant; at least one antigen; up to about 0.1% of a preservative; and saline or water or a mixture thereof.

The macrolide compounds useful in the invention include macrocyclic lactone compounds, milbemycin compounds, avermectin compounds and mixtures thereof described below.

The macrocyclic compounds include but are not limited to those described in U.S. Pat. Nos. 5,019,589; 4,886,828; 5,108,992; 5,030,650 and 5,055,486, incorporated herein by reference.

The preferred macrocyclic lactone compounds include the compounds designated LL-F28249α-λ which are (collectively) isolates from the fermentation broth of the microorganism *Streptomyces cyaneogriseus* subspecies *noncyanogenus*, deposited in the NRRL under deposit accession No. 15773. The method for preparation of LL-F28249α is disclosed in U.S. Pat. No. 5,106,994 and its continuation, U.S. Pat. No. 5,169,956, incorporated herein by reference.

The LL-F28249α-λ compounds are represented by the following structural formula:

| LL-F28249 | R₁ | R₂ | R₃ | R₄ | R₅ | R₆ | R₅ + R₆ | A–B | B–C |
|---|---|---|---|---|---|---|---|---|---|
| alpha | CH(CH₃)₂ | H | CH₃ | CH₃ | | | —O—CH₂— | CH—CH | CH=C |
| beta | CH₃ | H | CH₃ | CH₃ | | | —O—CH₂— | CH—CH | CH=C |
| gamma | CH₃ | CH₃ | CH₃ | CH₃ | | | —O—CH₂— | CH—CH | CH=C |
| delta | CH₃ | CH₃ | CH₃ | CH₃ | OH | CH₂OH | | CH—CH | CH=C |
| epsilon | CH(CH₃)₂ | H | H | CH₃ | | | —O—CH₂— | CH—CH | CH=C |
| zeta | CH₂CH₃ | H | CH₃ | CH₃ | | | —O—CH₂— | CH—CH | CH=C |
| eta | CH(CH₃)₂ | H | CH₃ | CH₃ | | | —O—CH₂— | C=CH | CH—CH |
| theta | CH(CH₃)₂ | H | CH₃ | CH₂CH₃ | | | —O—CH₂— | CH—CH | CH=C |
| iota | CH(CH₃)₂ | H | CH₂CH₃ | CH₃ | | | —O—CH₂— | CH—CH | CH=C |
| kappa | CH₃ | CH₃ | CH₃ | CH₃ | H | CH₃ | | CH—CH | CH=C |
| lambda | CH(CH₃)₂ | CH₃ | CH₃ | CH₃ | | | —O—CH₂— | CH—CH | CH=C |

The 23-oxo and 23-imino derivatives of LL-F28249α-λ compounds, useful in the stable vaccine compositions of this invention, are disclosed in U.S. Pat. No. 4,916,154, incorporated herein by reference.

A preferred LL-F28249α-λ compound and 23-imino derivative of an LL-F28249α-λ compound useful in the vaccine compositions of this invention have the following structural formulas:

LL-F28249α and
23-(O-methyloxime)-LL-F28249α (moxidectin)

Milbemycin compounds suitable for use in the stable vaccine compositions of this invention include but are not limited to milbemycin D, milbemycin oxime and those compounds described in U.S. Patent Nos. 3,950,360 and 4,346,171 and 4,547,520, incorporated herein by reference. Preferred milbemycin compounds for use in this invention are milbemycin D and milbemycin oxime.

Avermectin compounds which are suitable for use in the invention compositions include but are not limited to abamectin, ivermectin, doramectin and those compounds described in U.S. Pat. Nos. 4,199,569 and 4,310,519, incorporated herein by reference, with ivermectin, abamectin and doramectin being preferred. Doramectin and a method for its preparation are described in U.S. Pat. No. 5,089,480, incorporated herein by reference.

Antigens suitable for use in the compositions of the present invention include antigens derived from bacterial and viral pathogens of warm-blooded animals including but not limited to those derived by recombinant DNA technology. Preferred antigens include *Clostridium perfringens* type A, B, C and D, *Clostridium septicum, Clostridium tetani, Clostridium chauvoei, Clostridium novyi* type B, *Clostridium sordelli, Clostridium haemolytica, Pasteurella, Pasteurella maltocida* and *Corynebacterium pseudotuberculosis* which are used in the treatment of diseases such as Lamb dysentery, Pulpy Kidney disease (enterotoxaemia), Malignant Oedema (blood poisoning), Tetanus, Blackleg disease, Black disease, caseous lymphadenitis, and pasteurellosis.

The present invention also provides a process for the preparation of the stable vaccine compositions which comprises:

a) blending a dispersing agent with water to form a first solution;

b) adding to the first solution, a second solution comprising a macrolide compound as defined above or mixtures thereof in a water soluble organic solvent to form a third solution;

c) adding the third solution to a first suspension comprising at least one antigen, an adjuvant and a saline solution to form a second suspension; and d) adjusting the pH of the second suspension to about pH 6 to pH 7.

Dispersing agents useful in the process of the present invention include polyethylene oxide sorbitan mono-oleates such as polyoxyethylene (20) sorbitan mono-oleate (TWEEN®80, Harcros Chemicals), polyoxyethylene alcohols such as laureth 9 and cetomacrogol 1000, sodium lauryl sulfate, dioctyl sodium sulfosuccinate, polyethylene glycols, and α-hydro-ω-hydroxypoly(oxyethylene) poly (oxypropylene)poly(oxyethylene)block copolymers with polyethylene oxide sorbitan mono-oleates such as polyoxyethylene (20) sorbitan mono-oleate being preferred.

Surprisingly, it has now been found that warm-blooded animals which are treated with the vaccine compositions of the present invention (which contain a dispersing agent) respond to vaccination as well as warm-blooded animals treated with traditional vaccine compositions. This is an especially unobvious result because the invention compositions contain a dispersing agent which is generally believed to denature or otherwise disrupt antigens.

Further, it has been found that there is no deleterious effect on the bioavability and performance of the macrolide compound in the compositions of the invention.

The water soluble organic solvent is used to solubilize the macrolide compound. Water soluble organic solvents suitable for use in the present invention include alcohols such as benzyl alcohol, ethanol and methanol, propylene glycols and glycerol formal with benzyl alcohol being preferred.

The adjuvant of the invention is used to stabilize the antigens. Adjuvants suitable for use in the compositions of the present invention include aluminum hydroxide, potassium alum, protamine, aluminum phosphate and calcium phosphate with an aluminum hydroxide gel such as TAS-GEL® (Pitman-Moore, New Zealand) being preferred.

The pH of the second suspension is preferably adjusted to a pH value of about pH 6 to pH 7 with a mineral acid such as sulfuric acid, hydrochloric acid and hydrobromic acid. The pH is adjusted to that range because, in general, at pH values of less than pH 6 or greater than pH 7, denaturing of the antigens may occur.

In a preferred process of the present invention, a preservative is added to the second suspension prior to step (d). Preservatives suitable for use in the present invention include thimerosal ([(o-carboxyphenyl)-thio]ethylmercury sodium salt), formaldehyde, phenol, propylene glycol, glycerol, esters of p-hydroxybenzoic acid, benzoic acid and sodium benzoate with thimerosal being preferred.

In another preferred process of the invention, steps (a) and (b) are conducted at an elevated temperature (>25° C.) to ensure that the dispersing agent, macrolide compound and water soluble organic solvent are solubilized.

In the process of this invention, the first solution preferably comprises on a weight basis about 10% to 25% of the dispersing agent, the second solution comprises on a weight basis about 20% to 40% of the macrolide compound, and the first suspension comprises on a weight basis about 25% to 75% of the adjuvant.

The present invention further provides a stable macrolide composition for parenteral administration. The macrolide composition comprises on a weight to volume basis about 0.05% to 2.5% of a macrolide compound as defined above or mixtures thereof; about 0.1% to 10% of a water soluble organic solvent; about 1% to 8% of a dispersing agent; about 10% to 50% of an adjuvant and saline or water or a mixture thereof. Preferred macrolide compositions of the present invention comprise on a weight to volume basis, about 0.1% to 1% of an LL-F28249α-λ compound, a 23-oxo or 23-imino derivative of an LL-F28249α-λ compound, a milbemycin compound, an avermectin compound or mixtures thereof; about 0.2% to 2.5% of a water soluble organic solvent; about 2% to 7% of a dispersing agent; about 20% to 40% of an adjuvant; at least one antigen; up to about 0.1% of a preservative; and saline or water or a mixture thereof.

The stable macrolide compositions of this invention may be prepared by blending a solution of the macrolide compound, water soluble organic solvent, dispersing agent, adjuvant with water or a saline solution.

When parenterally administered, the vaccine compositions of this invention are highly effective for preventing or controlling helminthiasis, infection by acarids and arthropod endo- and ectoparasites and disease in warm-blooded animals such as sheep, cattle, horses, swine, deer, camels, poultry, dogs, cats and goats. Accordingly, the present invention provides a method for preventing or controlling helminthiasis, infection by acarids and arthropod endo- and ectoparasites and disease in warm-blooded animals which comprises parenterally administering to the animals an effective amount of a vaccine composition of the present invention.

Helminthiasis is a widespread disease found in many animals and is responsible for significant economic losses throughout the world. Among the helminths most frequently encountered are the group of worms referred to as nematodes. The nematodes are found in the intestinal tract, heart, lungs, blood vessels and other body tissues of animals and are a primary cause of anemia, weight loss and malnutrition in the infected animals. They do serious damage to the walls and tissue of the organs in which they reside and, if left untreated, may result in death to the infected animals.

The nematodes most commonly found to be the infecting agents of ruminants include Haemonchus and Ostertagia generally found in the abomasum; Cooperia, Trichostrongylus and Nematodirus generally found in the intestinal tract, and Dictyocaulus found in the lungs. In non-ruminant animals important nematodes include Toxocara and Ancylostoma in the intestine and Dirofilaria in the heart of dogs; Ascaris in the intestine of swine; Ascaridia and Heterakis in the intestine of poultry; and large and small strongyles in equines.

Arthropod ectoparasites commonly infecting warm-blooded animals include ticks, mites, lice, fleas, blowfly, the ectoparasite Lucilia sp. of sheep, biting insects and migrating dipterous larvae such as Hypoderma sp. in cattle, Gastrophilus in horses and Cuterebra sp. in rodents.

Treatment of animals to prevent infestation thereof by the above or to reduce or control the proliferation of these infecting agents in animals is thus an important and desirable advantage of the present invention.

In order to facilitate a further understanding of the invention, the following examples are presented primarily for the purpose of illustrating more specific details thereof. The invention is not to be deemed limited thereby except as defined in the claims.

EXAMPLE 1

Preparation of Moxidectin/6 in 1 Vaccine Compositions

The moxidectin/6 in 1 vaccine composition identified as composition number 1 in Table I is prepared by blending TASGEL® (300 mL) with normal saline solution (332.5 mL), adding the appropriate antigen concentrates in the amounts identified below, adding a moxidectin solution (previously prepared by blending a 30% wt/wt moxidectin in benzyl alcohol solution (7.5 mL) with a 17% wt/wt TWEEN®80 solution (300 mL) at about 37° C., and filtering and cooling the resultant solution), adding a 1.3% wt/wt thimerosal solution (7.7 mL), and adjusting the pH to about pH 6.5 with sulfuric acid.

| Antigen Concentrate | Amount (mL) |
| --- | --- |
| Cl. Septicum | 4.4 |
| Cl. novyi B | 1.8 |
| Cl. tetani | 1.85 |
| Cl. perfringens D | 40.5 |
| Cl. chauvoei | 8.75 |
| C. pseudotuberculosis | 2.5 |

Using essentially the same procedure, the moxidectin/6 in 1 vaccine compositions identified as composition numbers 2, 3 and 4 in Table I are obtained.

TABLE I

Moxidectin/6 in 1 Vaccine Compositions

| | Amount (% wt/v) | | | |
| --- | --- | --- | --- | --- |
| Component | Comp. Number 1 | Comp. Number 2 | Comp. Number 3 | Comp. Number 4 |
| Moxidectin (tech.) | 0.23 | 0.44 | 0.25 | 0.53 |
| Benzyl Alcohol | 0.53 | 1.03 | 0.59 | 1.23 |
| TWEEN ® 80 | 4.97 | 4.90 | 4.96 | 4.80 |
| Water | 25.04 | 25.33 | 25.14 | 24.39 |
| TASGEL ® | 30.00 | 29.53 | 30.00 | 30.00 |
| Normal Saline | 33.25 | 32.87 | 34.52 | 34.50 |
| Thimerosal | 0.01 | 0.01 | 0.01 | 0.01 |
| Cl. septicum concentrate | 0.44 | 0.43 | 0.60 | 0.60 |
| Cl. novyi B concentrate | 0.18 | 0.18 | 0.67 | 0.67 |
| Cl. tetani concentrate | 0.19 | 0.18 | 0.14 | 0.14 |
| Cl. perfringens D concentrate | 4.05 | 3.99 | 1.28 | 1.28 |
| Cl. chauvoei concentrate | 0.88 | 0.86 | 1.57 | 1.57 |
| C. pseudotuberculosis concentrate | 0.25 | 0.25 | 0.26 | 0.26 |

Commercially available 6 in 1 vaccines manufactured by Arthur Webster Pty Limited, Castle Hill, New South Wales, Australia are prepared using essentially the same procedure as described above, except that the moxidectin solution is not used. The 6 in 1 vaccines used in the following examples are identified as composition numbers 5, 6 and 7 in Table II.

TABLE II 6 in 1 Vaccines

| | Amount (% wt/v) | | |
| --- | --- | --- | --- |
| Component | Composition Number 5 | Composition Number 6 | Composition Number 7 |
| Water | 0.76 | 0.71 | 0.94 |
| TASGEL ® | 30.00 | 29.97 | 30.00 |
| Normal Saline | 63.25 | 63.33 | 64.50 |
| Thimerosal | 0.01 | 0.01 | 0.01 |
| Cl. septicum concentrate | 0.44 | 0.44 | 0.60 |
| Cl. novyi B concentrate | 0.18 | 0.18 | 0.67 |
| Cl. tetani concentrate | 0.19 | 0.19 | 0.14 |
| Cl. perfringens D concentrate | 4.05 | 4.05 | 1.28 |
| Cl. chauvoei concentrate | 0.88 | 0.87 | 1.57 |
| C. pseudotuberculosis concentrate | 0.25 | 0.25 | 0.26 |

EXAMPLE 2

Evaluation of fecal nematode egg counts, seroconversion to clostridial antigens and bodyweights of lambs treated with a moxidectin/6 in 1 vaccine composition One hundred eighty-five, two to four month old crossbred merino lambs at weaning which received a primary 6 in 1 vaccination (2 mL of composition number 5 from Table II) six weeks earlier are used in this trial. A single dose (2 mL) of a moxidectin/6 in 1 vaccine (composition number 1 from Table I) is administered to 92 lambs on trial day 0, and 93 lambs receive a single dose (2 mL) of a 6 in 1 vaccine (composition number 5 from Table II). Both treatments are administered subcutaneously high on the right side of the neck.

The lambs are weighed on days 0, 13 and 28 of the trial, at which time fecal samples are taken from the rectum of 15 lambs in both groups. These same lambs are blood sampled on days 0 and 28.

Fecal samples are evaluated for total nematode egg counts by microscopic examination. Pooled serum samples are assayed for antibody against Clostridium septicum, tetani and novyi type B exotoxins by serum neutralization testing in mice. Day 0 (pretreatment) samples from both groups are pooled for antibody analyses. The results are summarized in Tables III, IV and V.

As can be seen from the data in Table III, the moxidectin/6 in 1 vaccine (composition number 1) is highly effective in controlling nematodes. In the group receiving the 6 in 1 vaccine only, the worm burden rises sharply after weaning, while the egg count for the moxidectin/6 in 1 vaccine treated group falls to a low level by the first post-treatment sampling and the count remains low to the final sampling on day 28. This is an especially advantageous finding because the lambs receiving the moxidectin/6 in 1 vaccine maintain a low worm burden despite grazing as one mob on the same contaminated pasture as the 6 in 1 treated group.

Suprisingly, the lambs treated with the moxidectin/6 in 1 vaccine respond as well to vaccination as the lambs treated with the conventional 6 in 1 vaccine (Table IV).

TABLE III

Fecal Nematode Egg Counts (eggs per gram[1])

| Treatment | Day 0 | | Day 13 | | Day 28 | |
| --- | --- | --- | --- | --- | --- | --- |
| | Strongyle | Nematodirus spp | Strongyle | Nematodirus spp | Strongyle | Nematodirus spp |
| Moxidectin/ 6 in 1 vaccine | 259.9 | 19.7 | 0.3 | 1.4 | 0.3 | 4.9 |
| 6 in 1 vaccine | 165.6 | 6.5 | 257.4 | 41.6 | 644.2 | 90.0 |

[1]group geometric means

TABLE IV

Seroconversion to Clostridial Antigens

| | Titer (U/mL) | | |
| --- | --- | --- | --- |
| Antigen | Day 0 (pool) | Day 28 moxidectin/6 in 1 | Day 28 6 in 1 |
| Cl. Septicum | <2.0 | 2.25 | <2.0 |
| Cl. novyi B | <2.2 | 27.5–33 | 22–27.5 |
| Cl. tetani | <2.2 | 6.6–8.8 | 6.6–8.8 |

TABLE V

Bodyweights of Lambs

| | Mean Bodyweight (kg) | | |
| --- | --- | --- | --- |
| Treatment | Day 0 | Day 13 | Day 28 |
| Moxidectin/6 in 1 Vaccine | 26.2 | 27.8 | 29.6 |
| 6 in 1 Vaccine | 25.8 | 27.3 | 29.0 |

EXAMPLE 3

Evaluation of fecal nematode egg counts and seroconversion to clostridial antigens of ewes treated with a moxidectin/6 in 1 vaccine composition.

A group of 188 pregnant merino ewes between 2 and 5 years of age which are due to commence lambing approximately a fortnight after the start of the trial are used. They had been immunized annually with a 6 in 1 vaccine (Glanvac, CSL Ltd.) and had last been drenched two months prior to the trial with levamisole (Nilverm, Coopers Animal Health).

The ewes are weighed at day 0, when their average weight is 50.7 kg, and are randomly allocated into two groups. Ninety-four ewes receive a single dose (2 mL) of a moxidectin/6 in 1 vaccine (composition number 2 from Table I) on trial day 0, while 94 ewes receive a single dose of a 6 in 1 vaccine (composition number 6 from Table II). Fifteen ewes from each group are marked as monitors for fecal and blood sampling on days 0 and 24 of the trial and for a further fecal sample on day 15. Fecal and serum samples are tested as described in Example 2.

Since the trial is undertaken on a commercial property it is not possible to maintain the 6 in 1 treated ewes without nematode treatment beyond trial day 24, so those animals are treated with 7 mL of CYDECTIN® oral drench for sheep (Cyanamid Websters, Castle Hill, New South Wales, Australia) on day 25. No further treatment is administered to the animals that receive the moxidectin/6 in 1 vaccine at day 0. Further fecal samples are taken from the 15 monitor ewes in each group on days 38, 52 and 65 of the trial, and these samples are tested for egg counts as described above.

As can be seen from the data in Table VII, strong antibody responses are shown for both treatments. Advantageously, as can be seen from the data in Table VI, the moxidectin/6 in 1 treatment prevents the classical periparturient nematode egg rise in treated ewes even though they are grazing in pastures with the 6 in 1 treated ewes.

TABLE VI

Fecal Nematode Egg Counts (eggs per gram[1])

| | Moxidectin/6 in 1 Treated Ewes | | 6 in 1 Treated Ewes | |
| --- | --- | --- | --- | --- |
| Day | Strongyle | Nematodirus spp | Strongyle | Nematodirus spp |
| 0 | 32.9 | 0.3 | 34.6 | 0.8 |
| 13 | 0.3 | 0.3 | 284.1 | 2.2 |
| 24 | 0 | 0 | 233.6 | 0.9 |
| 36 | 0 | 0.3 | $0^2$ | $0^2$ |
| 52 | 13.4 | 0.7 | 6.3 | 0.3 |
| 65 | 32.9 | 0.7 | 30.3 | 0.3 |

[1]group geometric means
[2]6 in 1 treated ewes are treated with CYDECTIN® oral drench on day 25.

TABLE VII

Seroconversion to Clostridial Antigens

| | Titer (U/mL) | | |
| --- | --- | --- | --- |
| Antigen | Day 0 (pool) | Moxidectin/6 in 1 Treatment | 6 in 1 Treatment |
| Cl. septicum | <1.6 | 8 | 8–12 |
| Cl. novyi B | 2.2–3.3 | 16.5–22 | 22–33 |
| Cl. tetani | <2.2 | 8.8–11 | 11 |

EXAMPLE 4

Stability tests of Moxidectin/6 in 1 vaccine compositions

Moxidectin levels and antigen potencies for two of the invention moxidectin/6 in 1 vaccines (composition numbers 3 and 4 from Table I), and antigen potencies for a conventional 6 in 1 vaccine (composition number 7 from Table II) are measured after manufacture, and 6, 12 and 18 months after storage at 4° C. The antigen potencies are measured using the statutory assay procedures described in the British Pharmacopoeia (Veterinary) 1977. Moxidectin levels are determined by HPLC analysis. The results are summarized in Tables VIII, IX and X.

As can be seen from the data in Tables VIII and IX, the antigen potencies and moxidectin levels for composition numbers 3 and 4 remain within the specification requirements. This is an especially surprising discovery because all of the antigen components are proteins, and TWEEN®80 is known to denature proteins.

TABLE VIII

Stability Data For Moxidectin/6 in 1 Vaccine Composition Number 3

Component Levels
(U/mL except that moxidectin level is in % w/w)

| | | Time Held at 4° C. | | | |
|---|---|---|---|---|---|
| Component | Original | 6 Months | 12 Months | 18 Months | Specification |
| Cl. septicum | 2.3–5.4 | 3.4–5.8 | 3.7–5.5 | 5.5–6.3 | ≧2.5 |
| Cl. novyi B | 5–7 | 6–8 | 3.5–4.4 | 3.2–4.7 | ≧3.5 |
| Cl. tetani | 3.0–4.2 | 4.4–5.5 | 2.2–3.1 | 2–2.5 | ≧2.5 |
| Cl. perfringens D | 5.5–11 | 7.5–11 | 5.4–7.3 | 6–7.5 | ≧5 |
| Cl. chauvoei | 86 | 67 | 121 | 86 | ≧60 |
| C. pseudo-tuberculosis | 3.0 | 1.9 | 2.2 | 2.1 | ≧1.5 |
| Moxidectin | 0.22 | 0.22 | 0.22 | 0.22 | 0.21–0.25 |

TABLE IX

Stability Data For Moxidectin/6 in 1 Vaccine Composition Number 4

Component Levels
(U/mL except that moxidectin level is in % w/w)

| | | Time Held at 4° C. | | | |
|---|---|---|---|---|---|
| Component | Original | 6 Months | 12 Months | 18 Months | Specification |
| Cl. septicum | <1.8 | 3.1–5.6 | 4.2–6.3 | 4.2–6.3 | ≧2.5 |
| Cl. novyi B | 8–10 | 3.5–5.3 | 4.7–5.9 | | ≧3.5 |
| Cl. tetani | 4.8–7.2 | 3.6–5.5 | 2.0–3.0 | 2.2–2.9 | ≧2.5 |
| Cl. perfringens D | 16.5–22 | 10–11 | 6.2–9.4 | 5.0–6.0 | ≧5 |
| Cl. chauvoei | 92 | 85 | 128 | 115 | ≧60 |
| C. pseudo-tuberculosis | 6.2 | 1.9 | 2.6 | 2.3 | ≧1.5 |
| Moxidectin | 0.44 | 0.44 | 0.44 | 0.44 | 0.43–0.50 |

TABLE X

Stability Data for 6 in 1 Vaccine Composition Number 7

Component Levels (U/mL)

| | | Time Held at 4° C. | | | |
|---|---|---|---|---|---|
| Component | Original | 6 Months | 12 Months | 18 Months | Specification |
| Cl. septicum | 2.7 | NT | 5.1–7.6 | 5.1–7.6 | ≧2.5 |
| Cl. novyi B | 6.8 | NT | 3.5–5.3 | 5.1–7.7 | ≧3.5 |
| Cl. tetani | 2.4–3.6 | NT | 2.5–3.1 | 2.5–3.7 | ≧2.5 |
| Cl. perfringens D | 5.5–11 | NT | 4.2–6.2 | 9.0 | ≧5 |
| Cl. chauvoei | 93 | NT | 128 | 90 | ≧6.0 |
| C pseudo-tuberculosis | 4.6 | NT | 3.2 | 2.3 | ≧1.5 |
| Moxidectin | NA | NA | NA | NA | NA |

NT denotes not tested
NA denotes not applicable

We claim:

1. A vaccine composition consisting essentially on a weight to volume basis about 0.05% to 2.5% of a macrolide compound or mixtures of macrolide compounds; about 0.1% to 6% of a water-soluble organic solvent; about 1% to 8% of a dispersing agent; about 10% to 50% of an adjuvant; at least one antigen; up to about 0.1% of a preservative; and saline or water or a mixture thereof.

2. The vaccine composition according to claim 1 wherein the macrolide compound is selected from the group consisting of an LL-F28249α-λ, a 23-oxo or 23-imino derivative of an LL-F28249α-λ, a milbemycin, an avermectin and mixtures thereof.

3. The vaccine composition according to claim 2 which comprises on a weight to volume basis about 0.1% to 1% of the macrolide compound or mixtures of macrolide compounds; about 0.2% to 2.5% of the water-soluble organic solvent; about 2% to 7% of the dispersing agent; and about 20% to 40% of the adjuvant.

4. The vaccine composition according to claim 1 wherein the macrolide compound is selected from the group consisting of LL-F28249α, moxidectin, milbemycin D, milbemycin oxime, ivermectin, abamectin and doramectin.

5. The vaccine composition according to claim 4 wherein the macrolide compound is moxidectin.

6. The vaccine composition according to claim 1 wherein the water-soluble organic solvent is selected from the group consisting of benzyl alcohol, methanol, ethanol, a propylene glycol and glycerol formal.

7. The vaccine composition according to claim 6 wherein the water-soluble organic solvent is benzyl alcohol.

8. The vaccine composition according to claim 1 wherein the dispersing agent is selected form the group consisting of a polyethylene oxide sorbitan mono-oleate, a polyoxyethylene alcohol, sodium lauryl sulfate, dioctyl sodium sulfosuccinate, a propylene glycol and an α-hydro-ω-hydroxypoly(oxyethylene)poly(oxypropylene)poly(oxyethylene) block copolymer.

9. The vaccine composition according to claim 8 wherein the dispersing agent is polyoxyethylene (20) sorbitan mono-oleate.

10. The vaccine composition according to claim 1 wherein the adjuvant is selected from the group consisting of aluminum hydroxide, potassium alum, protamine, aluminum phosphate and calcium phosphate.

11. The vaccine composition according to claim 1 wherein the adjuvant is an aluminum hydroxide gel.

12. The vaccine composition according to claim 1 which comprises at least one antigen selected from the group consisting of *Clostridium perfringens* type A, B, C and D, *Clostridium septicum, Clostridium tetani, Clostridium chauvoei, Clostridium novyi* type B, *Clostridium sordelli, Clostridium haemolytica, Pasteurella haemolytica, Pasteurella maltocida* and *Corynebacterium pseudotuberculosis.*

13. The vaccine composition according to claim 12 which comprises *Clostridium perfringens* type D, *Clostridium septicum, Clostridium tetani, Clostridium chauvoei, Clostridium novyi* type B and *Corynebacterium pseudotuberculosis.*

14. The vaccine composition according to claim 1 wherein the preservative is selected from the group consisting of thimerosal, formaldehyde, phenol, propylene glycol, glycerol, esters of p-hydroxybenzoic acid, benzoic acid and sodium benzoate.

15. The vaccine composition according to claim 14 wherein the preservative is thimerosal.

16. The vaccine composition according to claim 1 wherein the pH of the composition is about pH 6 to pH 7.

17. The vaccine composition according to claim 1 wherein the macrolide compound is moxidectin, the water-soluble organic solvent is benzyl alcohol and the adjuvant is aluminum hydroxide gel.

18. The vaccine composition according to claim 17 which further comprises *Clostridium perfringens* type D, *Clostridium septicum, Clostridium tetani, Clostridium chauvoei, Clostridium novyi* type B and *Corynebacterium pseudotuberculosis.*

* * * * *